(12) United States Patent
Adam et al.

(10) Patent No.: US 7,041,143 B2
(45) Date of Patent: *May 9, 2006

(54) METHOD OF COLORING POROUS MATERIAL

(75) Inventors: Jean-Marie Adam, Rosenau (FR); Taher Yousaf, Basel (CH); Beate Fröhling, Steinen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/469,619

(22) PCT Filed: Feb. 28, 2002

(86) PCT No.: PCT/EP02/02146

§ 371 (c)(1),
(2), (4) Date: Sep. 3, 2003

(87) PCT Pub. No.: WO02/069920

PCT Pub. Date: Sep. 12, 2002

(65) Prior Publication Data

US 2004/0083560 A1 May 6, 2004

(30) Foreign Application Priority Data

Mar. 8, 2001 (EP) .................................. 01810240

(51) Int. Cl.
*A61K 7/13* (2006.01)
*D06P 1/02* (2006.01)
(52) U.S. Cl. .................................. 8/429; 8/405; 8/666
(58) Field of Classification Search .................... 8/666, 8/405, 429
See application file for complete search history.

(56) References Cited

U.S. PATENT DOCUMENTS

| | | | |
|---|---|---|---|
| 1,882,556 A | 10/1932 | Hentrich et al. | |
| 1,882,562 A * | 10/1932 | Glietenberg et al. | 534/550 |
| 2,065,593 A * | 12/1936 | Lubs | 534/550 |
| 2,926,986 A | 3/1960 | Petitcolas et al. | 8/45 |
| 3,369,970 A | 2/1968 | McLaughlin et al. | 167/88 |
| 3,502,424 A * | 3/1970 | Hertel et al. | 8/598 |
| 3,502,425 A * | 3/1970 | Hertel et al. | 8/598 |
| 3,526,479 A * | 9/1970 | Lange et al. | 436/97 |
| 4,168,952 A | 9/1979 | Bühler et al. | 8/10.1 |
| 4,268,600 A | 5/1981 | Robillard et al. | 430/142 |
| 4,964,874 A | 10/1990 | Saphakkul | 8/429 |
| 5,135,543 A | 8/1992 | Chan et al. | 8/405 |
| 5,169,403 A | 12/1992 | Chan et al. | 8/405 |
| 5,256,823 A | 10/1993 | Chan et al. | 564/284 |
| 5,294,726 A | 3/1994 | Behler et al. | 554/98 |
| 5,298,029 A | 3/1994 | Chan et al. | 8/405 |
| 5,360,930 A | 11/1994 | Chan et al. | 564/284 |
| 5,708,151 A | 1/1998 | Möckli | 534/608 |
| 5,879,412 A | 3/1999 | Rondeau et al. | 8/411 |
| 5,919,273 A | 7/1999 | Rondeau et al. | 8/412 |
| 5,980,587 A | 11/1999 | Samain | 8/426 |
| 5,993,490 A | 11/1999 | Rondeau et al. | 8/409 |
| 6,001,135 A | 12/1999 | Rondeau et al. | 8/407 |
| 6,190,421 B1 * | 2/2001 | Rondeau et al. | 8/407 |
| 6,228,129 B1 | 5/2001 | De la Mettrie et al. | 8/401 |
| 6,248,314 B1 | 6/2001 | Nakashimada et al. | 424/70.11 |
| 6,436,153 B1 | 8/2002 | Rondeau | 8/426 |

FOREIGN PATENT DOCUMENTS

| | | |
|---|---|---|
| DE | 1131641 | 6/1962 |
| DE | 1213374 | 3/1966 |
| DE | 2807780 | 8/1978 |
| DE | 2923261 | 12/1980 |
| DE | 19729080 | 11/1998 |
| EP | 0312343 | 4/1989 |
| EP | 0318294 | 5/1989 |
| EP | 0758547 | 2/1997 |
| EP | 0801942 | 10/1997 |
| EP | 0818193 | 1/1998 |
| EP | 0819422 | 1/1998 |
| EP | 0834303 | 4/1998 |
| GB | 900402 | 7/1962 |
| GB | 2319776 | 6/1998 |
| NL | 6414335 | * 7/1965 |
| WO | 90/01922 | 3/1990 |
| WO | 95/01772 | 1/1995 |
| WO | 95/15144 | 6/1995 |
| WO | 99/36034 | 7/1999 |
| WO | 99/40895 | 8/1999 |
| WO | 01/66646 | 9/2001 |

OTHER PUBLICATIONS

STN abstract of NL 6414335.*
Derwent Abstract 97-515049/48 for EP 801942 (1997).
Derwent Abstract 98-584726/50 for DE 19729080 (1998).
Derwent Abstract 1999-508573/42 for WO 99/40895 (1999), Aug. 1999.
Derwent Abstract 89-228595/32 for DE 3829102 (1989).
Chem. Abstr. 1967:509619 for DE 1213374 (1966).

* cited by examiner (Continued)

Primary Examiner—Margaret Einsmann
(74) Attorney, Agent, or Firm—Kevin T. Mansfield

(57) ABSTRACT

A method of coloring porous material, especially human hair, is described, which method comprises applying to the material being colored, in any desired order successively, or simultaneously, a) a capped diazonium compound and b) a water-soluble coupling component under conditions such that, initially, coupling does not take place, and then causing the capped diazonium compound present on the material to react with the coupling component.

10 Claims, No Drawings

METHOD OF COLORING POROUS MATERIAL

The present invention relates to a method of colouring porous material, for example metal, wood or keratin-containing fibres, especially human hair, using developing dyes, that is to say dyes which are formed inside the pores of the substrate.

Colouring with the aid of developing dyes has been known for a long time and has also been generally used for dyeing cotton. The dyes and the colouring methods used therefore do not, however, provide satisfactory results for colouring hair.

For colouring hair, therefore, oxidation dyes are used in most cases; however, they too are not capable of satisfying all requirements. The fastness to washing properties are often inadequate and, in addition, the colouring conditions required often cause a greater or lesser amount of damage to the hair. There has therefore been a need for a colouring method which does not have the mentioned disadvantages or which has them to an insignificant degree.

The present invention relates to a method of colouring porous material, which comprises applying to the material being coloured, in any desired order successively, or simultaneously, a) a capped diazonium compound and
b) a water-soluble coupling component under conditions such that, initially, coupling does not take place, and then causing the capped diazonium compound present on the material to react with the coupling component.

The colorations obtained are distinguished by outstanding fastness to washing properties, which are significantly better than in the case of colorations with oxidation dyes, and there is virtually no damage to the hair. Moreover, there is no staining of the scalp, because the dye components do not penetrate into the skin and non-fixed dye can be washed off readily.

Suitable capped diazonium compounds include, for example, antidiazoates of formula

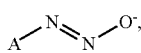

(1)

diazosulfonates of formula

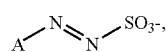

(2)

diazines of formula

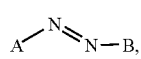

(3)

and also cyclic triazenes of formula

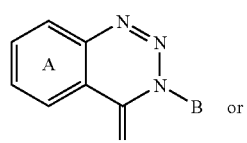

(4)

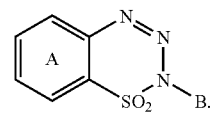

(5)

In formulae (1) to (5):
A is the organic residue of an unsubstituted or substituted aromatic or heterocyclic amine,
B is the radical of an unsubstituted or substituted, water-soluble aliphatic or aromatic amine and
R is an unsubstituted or substituted alkyl group,
wherein at least one of the groups must contain a radical imparting water solubility.

Suitable radicals imparting water solubility include, for example, $SO_3H$, COOH, OH or a quaternised ammonium radical of formula

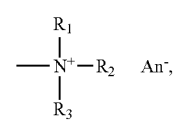

(6)

wherein $R_1$, $R_2$ and $R_3$ are each independently of the others unsubstituted or substituted alkyl and An is an anion.

According to the invention, alkyl groups R, $R_1$, $R_2$ and $R_3$ are to be understood as being generally open-chain or branched alkyl radicals, for example methyl, ethyl, n- or iso-propyl and n-, sec- or tert-butyl.

Such alkyl radicals may be mono- or poly-substituted, for example by hydroxy, carboxy, halogen, cyano or by $C_1$–$C_4$alkoxy.

Preferably, the alkyl groups are unsubstituted and each has from 1 to 4, especially 1 or 2, carbon atoms.

Suitable anions An are both inorganic and organic anions, for example halide, such as chloride, bromide or iodide, sulfate, hydrogen sulfate, methyl sulfate, formate, acetate and lactate.

The anion is generally determined by the preparation process. Preferably, the chlorides, hydrogen sulfates, sulfates, methosulfates or acetates are present.

A is the radical of an unsubstituted or substituted aromatic or heterocyclic amine. For example, unsubstituted or substituted radicals of aminobenzene, 1- or 2-aminonaphthalene, 2-aminothiophene, 2-amino-1,3-thiazole, 5-amino-1,2-thiazole, 2-amino-1,3-benzothiazole, 1-amino-2,3-benzothiazole, 2-aminoimidazole, 2-amino-1,3,4-thiadiazole, 2-amino-1,3,5-thiadiazole, 2-amino-1,3,4-triazole, 3-, 7- or 8-aminopyrazole, 2-aminobenzimidazole, 2-aminobenzopyrazole, 2- or 4-aminopyridine, 2-, 3-, 4-, 7- or 8-aminoquinoline, 2-amino-pyrimidine and 3-aminoisoxazole, 5-aminoquinoline, 4-aminodiphenylamine, 2-aminodiphenyl ether and 4-aminoazobenzene are suitable.

Such radicals may be mono- or poly-substituted, for example by $C_1$–$C_4$alkyl, $C_1$–$C_4$alkoxy, $C_1$–$C_4$alkylthio, halogen, e.g. fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkylcarbonylamino, $C_1$–$C_4$alkoxysulfonyl or by di-(hydroxy-$C_1$–$C_4$alkyl)-aminosulfonyl.
Examples of suitable radicals A are as follows:
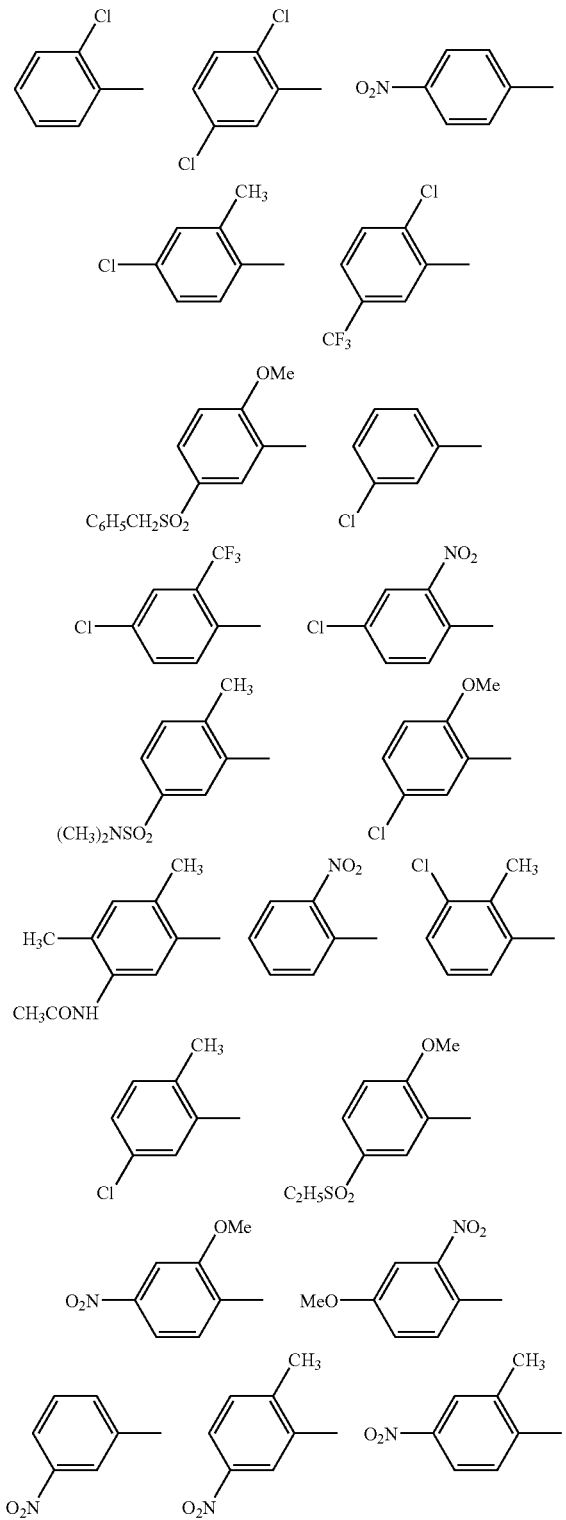
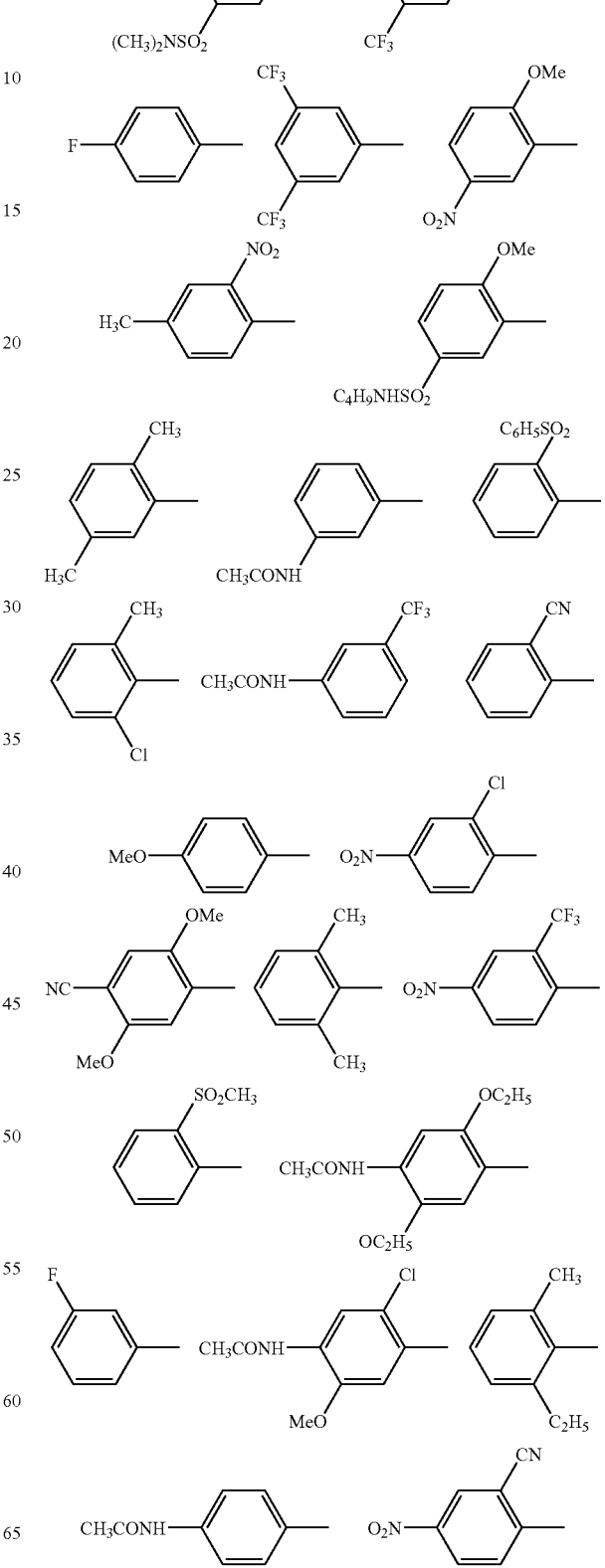

-continued

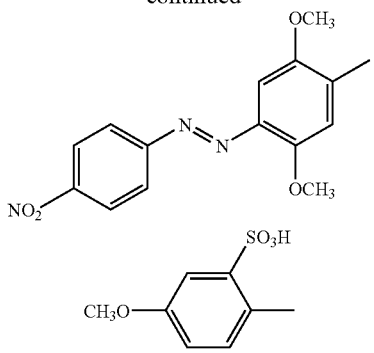

B is the radical of an unsubstituted or substituted, water-soluble aliphatic or aromatic amine, especially suitable aliphatic amines being those carrying a carboxylic acid or sulfonic acid group, for example methylaminoacetic acid (sarcosine), methylaminobutyric acid, methylaminopropionic acid, ethylaminoacetic acid, ethylaminobutyric acid, 1-methylamino-ethane-2-sulfonic acid, 1-ethylamino-ethane-2-sulfonic acid and 1-methylamino-propane-3-sulfonic acid are suitable.

Aromatic amines that are suitable for B are especially aniline and aminonaphthalene compounds, more especially those carrying a carboxylic acid or sulfonic acid group. The amino group of those compounds may be unsubstituted but is preferably substituted, for example by unsubstituted or substituted $C_1$–$C_4$alkyl. Suitable substituents in the latter case are especially hydroxy and carboxy. Suitable radicals of aromatic amines are, for example, as follows:

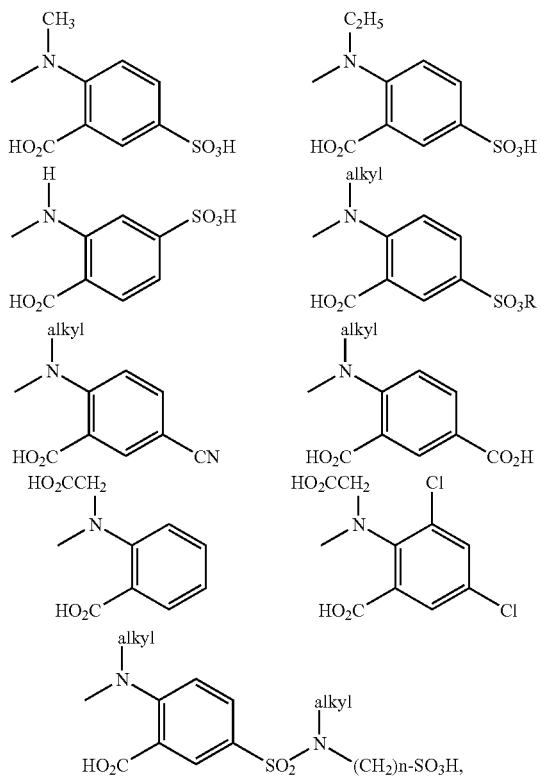

alkyl being as defined hereinbefore, especially methyl.

Suitable coupling components are, for example, the usual coupling components customarily used for azo dyes and known from the pertinent literature, e.g. coupling components from the benzene series, naphthalene series, open-chain methylene-active compounds (e.g. acylacetarylamides) and the heterocyclic series.

They are, for example, acylacetarylamides, phenols, naphthols, pyridones, quinolones, pyrazoles, indoles, diphenylamines, anilines, aminopyridines, pyrimidones, naphthylamines, aminothiazoles, thiophenes or hydroxypyridines.

Acetoacetanilides, phenols, anilines, diphenylamines, naphthylamines, indoles, quinolines, pyridones, pyrazoles and aminopyridines are especially suitable.

Such coupling components may carry further substituents, for example amino, alkylamino, dialkylamino, halogen, alkyl, alkoxy, aryl, especially phenyl or naphthyl, or aryloxy, but especially a group imparting water solubility, e.g. hydroxy, carboxy, sulfo or a quaternised ammonium radical of formula (6) defined hereinbefore.

The coupling components preferably carry one or two such groups imparting water solubility. Examples of suitable coupling components are as follows:

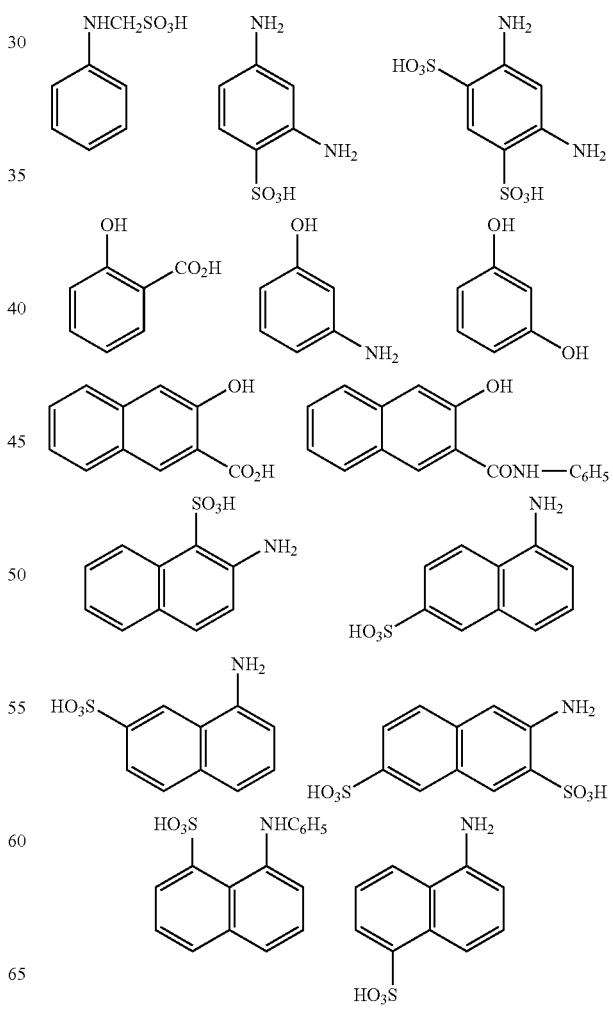

-continued
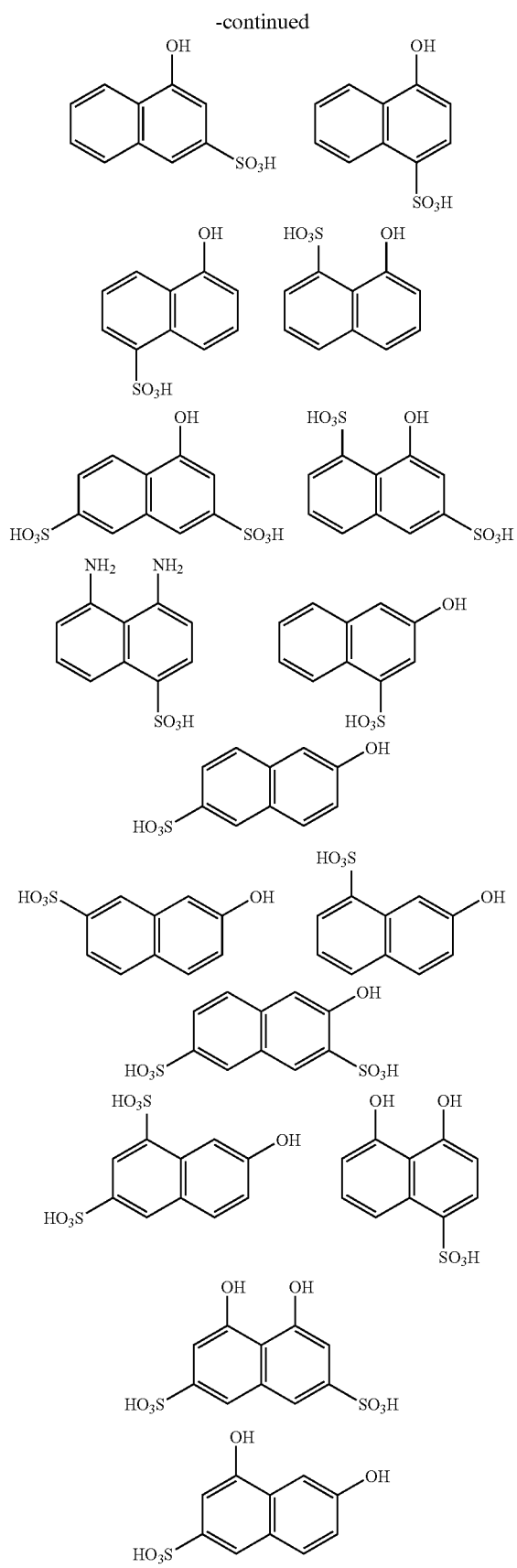
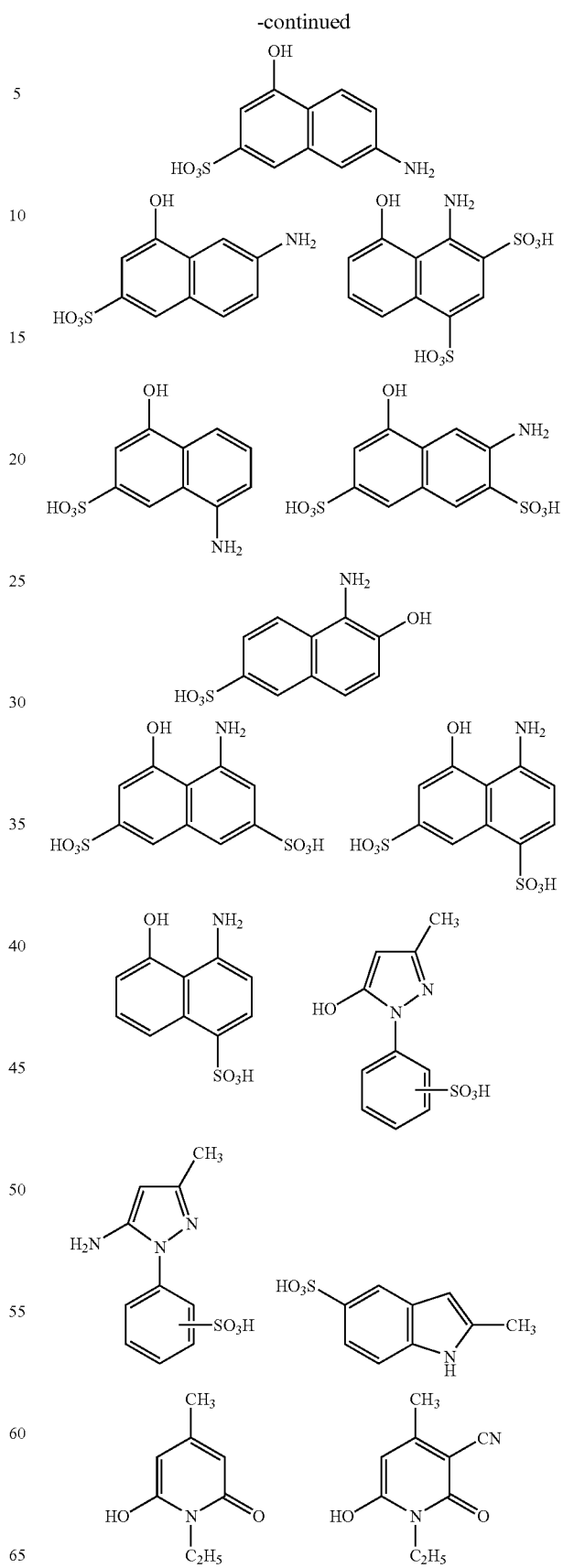

-continued

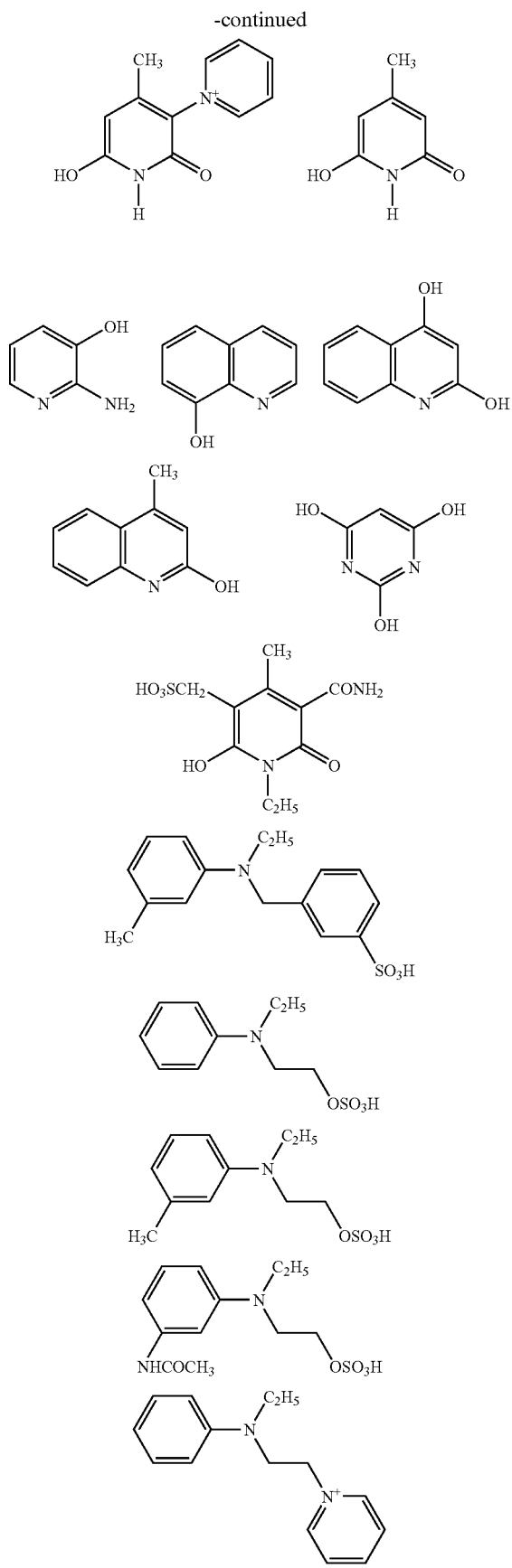

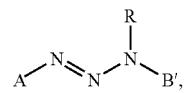

The amines of formulae A-NH$_2$ and B—NHR and the coupling components are known or can be synthesised in a manner known per se.

The compounds of formulae (1), (2), (4) and (5) are also known or can be synthesised in a manner known per se.

The compounds of formula (3) wherein B is the radical of an aliphatic amine are likewise known or can be synthesised in a manner known per se.

The compounds of formula $$A-N=N-N{\overset{R}{\underset{B'}{\,}}},\qquad(7)$$

wherein
A is the radical of an unsubstituted or substituted, water-soluble aromatic or heterocyclic amine,
B' is the radical of an unsubstituted or substituted, water-soluble aliphatic or aromatic amine and
R is an unsubstituted or substituted alkyl group, are novel.

The definitions and preferred meanings mentioned under formulae (1) to (5) apply to A and R, and the definitions and preferred meanings mentioned under formulae (1) to (5) apply to B', insofar as they refer to aromatic amines. The compounds of formula (7) can likewise be prepared in a manner known per se; for example, an amine of formula A-NH$_2$ is, in customary manner, diazotised and coupled to an amine of formula B'—NHR, there coming into consideration as amines B—NH$_2$ only those compounds that couple at the nitrogen atom rather than at a carbon atom of the aromatic ring. Such compounds are, preferably, aniline derivatives substituted in the 4-position.

The first stage of the colouring method according to the invention comprises applying to the material being coloured, in any desired order successively, or simultaneously, a capped diazonium compound and a water-soluble coupling component under conditions such that, initially, coupling does not take place. That is accomplished, for example, by immersing the material in a solution comprising the capped diazonium compound or the coupling component and then, optionally after rinsing and intermediate drying, immersing the material in a solution of the second component. Preferably, however, the capped diazonium compound and the coupling component are contained together in one solution. It is also possible for the solutions in question to be applied to the material by means of spraying or similar means, although it must be ensured that there is adequate penetration unless it is desired to colour only the upper layers. During that first stage the diazonium compound and the coupling component should not yet react with one another, which is achieved preferably by maintaining a pH of from 8 to 12, especially from 9 to 11.

In the second stage, the diazonium compound and the coupling component are then caused to react, preferably by lowering the pH to a value of from 5 to 2, especially from 3 to 4. Lowering the pH is achieved in conventional manner by adding an acid, such as tartaric acid or citric acid, a citric acid gel, a suitable buffer solution or by means of an acid dye.

The ratio of the amount of alkaline colouring composition applied in the first stage to that of acid colouring composition applied in the second stage is preferably about from 1:3 to 3:1, especially about 1:1.

The contact time is preferably about from five to thirty minutes in each case, especially from 10 to 20 minutes in each case.

The coloured material is then finished in customary manner, for example by rinsing with water and then drying.

The method according to the invention is suitable for all-over colouring of the hair, that is to say when colouring the hair on a first occasion, and also for re-colouring subsequently.

A preferred embodiment of the method according to the invention relates to the colouring of porous material by bringing the material being coloured into contact with a capped diazonium compound and a water-soluble coupling component, in any desired order successively, or simultaneously,

- a) under alkaline conditions and optionally in the presence of a further dye, preferably an oxidation dye, or a cationic, anionic or uncharged direct dye, especially a cationic dye selected from the group of the cationic dyes as described in WO 95/01772 and WO 01/66646 and then subjecting the material being coloured to treatment with acid, or
- b) under alkaline conditions, and then subjecting the material being coloured to treatment with acid, optionally in the presence of a further dye, preferably an oxidation dye, or a cationic, anionic or uncharged direct dye, especially a cationic dye selected from the group of the cationic dyes as described in WO 95/01772 and WO 01/66646, or
- c) under alkaline conditions in the presence of an oxidising agent, and optionally in the presence of a further dye, preferably an oxidation dye, or a cationic, anionic or uncharged direct dye, especially a cationic dye selected from the group of the cationic dyes as described in WO 95/01772 and WO 01/66646 and then subjecting the material being coloured to treatment with acid.

In the methods according to the invention, whether or not colouring is to be carried out in the presence of a further dye will depend upon the colour shade to be obtained.

In the context of the present invention, the expression "alkaline conditions" denotes a pH in the range from 8 to 10, preferably 9–10, especially 9.5–10.

The alkaline conditions are customarily achieved by adding bases, for example sodium carbonate, ammonia or sodium hydroxide, to the hair or to the dye precursors, the capped diazonium compound and/or the water-soluble coupling component, or to colouring compositions comprising the dye precursors.

In the context of the present invention, oxidising agents are understood to be any oxidising agent customarily used for oxidative hair colouring, for example dilute hydrogen peroxide solutions, hydrogen peroxide emulsions or hydrogen peroxide gels, alkaline earth metal peroxides, urea peroxides, melamine peroxides, especially dilute hydrogen peroxide solutions.

The oxidising agents are used in appropriate stoichiometric amounts that correspond to the total molar amounts of oxidation dye precursors.

The method according to the invention is used for colouring porous material, for example wood, glass fibres, aluminium, cotton, paper, natural or synthetic polyamides, e.g. leather, wool, nylon or perlon, but especially keratin-containing fibres and more especially for colouring hair. The hair may be the hair of wigs or, especially, the living hair of animals and, more especially, humans.

The invention relates also to colouring compositions for carrying out the method according to the invention, which compositions comprise a) a compound of formula (1), (2), (3), (4) or (5) indicated hereinbefore,
b) a medium for adjusting the pH,
c) water and, optionally,
d) further additives.

Preferred compositions comprise a) a compound of formula (1), (2), (3), (4) or (5) indicated hereinbefore,
b) a medium for adjusting the pH,
c) water,
d) a coupling component and, optionally,
e) further additives.

Especially preferred compositions comprise f) a compound of formula (1), (2), (3), (4) or (5) indicated hereinbefore,
g) a medium for adjusting the pH,
h) water,
i) a coupling component,
j) a further dye, preferably an oxidation dye, or a cationic, anionic or uncharged direct dye, especially a cationic dye selected from the group of the cationic dyes as described in WO 95/01772 and WO 01/66646, and, optionally,
k) further additives.

Special preference is given to colouring compositions for the colouring of hair. Further additives that are suitable for such compositions include additives that are customary in hair-colouring, for example further dyes, surfactants, solvents, perfumes, polymeric adjuvants, thickeners and light stabilisers.

The diversity of shades and the colour fastness of the dye mixtures used in accordance with the invention can be increased by combination with other dyes used in the field of hair-colouring compositions. They can be combined very readily both with oxidation dyes and with direct dyes, it being possible for the latter to be of anionic or cationic nature or uncharged.

In all colouring compositions, it is also possible for a plurality of different colourants to be used together; likewise, it is possible for a plurality of different oxidation dye precursors from the group of the developer and coupler compounds to be used together, for example aromatic compounds having a primary or secondary amino group, nitrogen-containing heterocycles, aromatic hydroxy compounds or amino acids, as described, for example, in German Patent Application 197 17 224.5.

The dye mixtures according to the invention produce colour shades in the range from yellow to blue, and the fastness properties are outstanding. Attention is drawn to the excellent fastness to light and fastness to washing properties and to their property that enables hair that has already been coloured a dark colour still to be distinctly altered in shade.

In a further embodiment, for the purpose of further modification of colour shades the colouring compositions according to the invention also comprise, in addition to the dye mixtures according to the invention, customary direct dyes, for example from the group of the nitroanilines, nitrophenylenediamines, nitroaminophenols, anthraquinones, indophenols, phenazines, phenothiazines and methines.

Also very suitable for combination with the dye mixtures according to the invention are cationised nitroaniline and anthraquinone dyes, for example those described in the following patent specifications: U.S. Pat. No. 5,298,029, U.S. Pat. No. 5,360,930, U.S. Pat. No. 5,169,403, U.S. Pat. No. 5,256,823, U.S. Pat. No. 5,135,543, EP-A-818 193, U.S. Pat. No. 5,486,629 and EP-A-758 547.

Also, cationic direct dyes such as cationic azo dyes, for example according to GB-A-2 319 776, as well as the oxazine dyes described in DE-A-299 12 327 and mixtures thereof with the other direct dyes mentioned therein, are likewise suitable for combination.

Cationic direct dyes, for example according to WO 95/01772, WO 95/15144, EP 714 954 and EP 318 294, are also suitable for combination.

In addition, the colouring compositions according to the invention may also comprise naturally occurring dyes, for example henna red, henna neutral, henna black, camomile blossom, sandalwood, black tea, Rhamnus frangula bark, sage, campeche wood, madder root, catechu, sedre and alkanet root. Such colouring methods are described, for example, in EP-A-404 868.

In respect of further customary dye components, reference is made expressly to the series "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250 (direct dyes), and chapter 8, pages 264–267 (oxidation dyes), and to "Europäisches Inventar der Kosmetikrohstoffe", 1996, published by The European Commission, obtainable in diskette form from the Bundesverband der deutschen Industrie- und Handelsunternehmen für Arzneimittel, Reformwaren und Körperpflegemittel e. V., Mannheim.

It is not necessary for the oxidation dye precursors, where present, or for the dyes each to be single compounds, but rather the colouring compositions according to the invention may additionally comprise, depending on the preparation procedures for the individual dyes, lesser amounts of further components, provided such components do not have an adverse effect on the colouring result or do not need to be excluded for other reasons, for example toxicological reasons.

The dye mixtures according to the invention may also readily be used in combination with other dyes and/or adjuvants used in the colouring of hair, for example with oxidising agents to achieve lightened colorations, as described in EP-A-810 851, oxidising agents in the form of permanent-wave fixing solution, as described in DE-A-197 13 698 or WO 99/40895, oxidation dyeing compositions, as described in EP-A-850 636, EP-A-850 637, EP-A-850 638 and EP-A-852 135, oxidation dyes in the presence of oxidoreductase enzyme, as described in WO 99/17730 and WO 99/36034, autooxidisable oxidation dyes, as described in WO 99/20234, or nitrobenzene derivatives, as described in WO 99/20235.

The colouring compositions according to the invention produce intense colorations even at physiologically tolerable temperatures of less than 45° C. They are accordingly suitable especially for colouring human hair. For use on human hair, the colouring compositions can usually be incorporated into an aqueous cosmetic carrier. Suitable aqueous cosmetic carriers include, for example, creams, emulsions, gels and also surfactant-containing foaming solutions, e.g. shampoos or other preparations, that are suitable for use on keratin-containing fibres. Such forms of use are described in detail in Research Disclosure 42448 (August 1999). If necessary, it is also possible to incorporate the colouring compositions into anhydrous carriers, as described, for example, in U.S. Pat. No. 3,369,970. The colouring compositions according to the invention are also outstandingly suitable for the colouring method described in DE-A-3 829 870 using a colouring comb or colouring brush.

The colouring compositions according to the invention may furthermore comprise any active ingredient, additive or adjuvant known for such preparations. The colouring compositions in many cases comprise at least one surfactant, there being suitable in principle anionic and also zwitterionic, ampholytic and non-ionic surfactants. In many cases, however, it has proved advantageous to select the surfactants from anionic and non-ionic surfactants.

Anionic surfactants suitable for use in preparations according to the invention include any anionic surface-active substance that is suitable for use on the human body. Such a substance is characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. Examples of suitable anionic surfactants, each in the form of sodium, potassium or ammonium salts or mono-, di- or tri-alkanolammonium salts having 2 or 3 carbon atoms in the alkanol group, are:

linear fatty acids having from 10 to 22 carbon atoms (soaps), ether carboxylic acids of formula R—O—($CH_2$—$CH_2$—O)$_x$—$CH_2$—COOH, in which R is a linear alkyl group having from 10 to 22 carbon atoms and x=0 or from 1 to 16, acyl sarcosides having from 10 to 18 carbon atoms in the acyl group, acyl taurides having from 10 to 18 carbon atoms in the acyl group, acyl isothionates having from 10 to 18 carbon atoms in the acyl group, sulfosuccinic acid mono- and di-alkyl esters having from 8 to 18 carbon atoms in the alkyl group and sulfosuccinic acid monoalkylpolyoxyethyl esters having from 8 to 18 carbon atoms in the alkyl group and from 1 to 6 oxyethyl groups, linear alkanesulfonates having from 12 to 18 carbon atoms, linear α-olefin sulfonates having from 12 to 18 carbon atoms, α-sulfo fatty acid methyl esters of fatty acids having from 12 to 18 carbon atoms, alkyl sulfates and alkyl polyglycol ether sulfates of formula R'—O($CH_2$—$CH_2$—O)$_{x'}$—$SO_3H$, in which R' is a preferably linear alkyl group having from 10 to 18 carbon atoms and x'=0 or from 1 to 12, mixtures of surface-active hydroxysulfonates according to DE-A-3 725 030, sulfated hydroxyalkylpolyethylene and/or hydroxyalkylenepropylene glycol ethers according to DE-A-3 723 354, sulfonates of unsaturated fatty acids having from 12 to 24 carbon atoms and from 1 to 6 double bonds according to DE-A-3 926 344, esters of tartaric acid and citric acid with alcohols that are addition products of approximately from 2 to 15 molecules of ethylene oxide and/or propylene oxide with fatty alcohols having from 8 to 22 carbon atoms.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated $C_8$–$C_{22}$carboxylic acids, such as oleic acid, stearic acid, isostearic acid and palmitic acid.

The term "zwitterionic surfactants" denotes surface-active compounds that carry at least one quaternary ammonium group and at least one —$COO^{(-)}$ or —$SO_3^{(-)}$ group in the molecule. Zwitterionic surfactants that are especially suitable are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyidimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocamidopropyl betaine.

Ampholytic surfactants are to be understood as meaning surface-active compounds that, in addition to a $C_8$–$C_{18}$-alkyl or -acyl group, contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$–$C_{18}$acylsarcosine.

Non-ionic surfactants contain as the hydrophilic group, for example, a polyol group, a polyalkylene glycol ether group or a combination of polyol and polyglycol ether groups.

Such compounds are, for example:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, $C_{12}$–$C_{22}$ fatty acid mono- and di-esters of addition products of from 1 to 30 mol of ethylene oxide with glycerol, $C_8$–$C_{22}$alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters, addition products of ethylene oxide with fatty acid alkanolamides.

The alkyl-group-containing compounds used as surfactants may be single substances, but the use as starting materials of natural raw materials of vegetable or animal origin is generally preferred in the preparation of such substances, with the result that the substance mixtures obtained have different alkyl chain lengths according to the particular starting material used.

The surfactants that are addition products of ethylene and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Examples of further active ingredients, adjuvants and additives are:

non-ionic polymers, for example vinylpyrrolidone/vinyl acrylate copolymers, polyvinyl pyrrolidone and vinylpyrrolidone/vinyl acetate copolymers and polysiloxanes, zwitterionic and amphoteric polymers, for example acrylamidopropyl-trimethylammonium chloride/acrylate copolymers and octylacrylamide/methyl methacrylate/tert-butylaminoethyl methacrylate/2-hydroxypropyl methacrylate copolymers, anionic polymers, for example polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers, thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such as amylose, amylopectin and dextrins, clays, e.g. bentonite or fully synthetic hydrocolloids such as, for example, polyvinyl alcohol, structuring agents, such as glucose and maleic acid, hair-conditioning compounds, such as phospholipids, for example soya lecithin, egg lecithin and cephalins, silicone oils, and also conditioning compounds, for example such as those described in DE-A-197 29 080, EP-A-834 303 or EP-A-312 343, protein hydrolysates, especially elastin, collagen, keratin, milk protein, soya protein and wheat protein hydrolysates, condensation products thereof with fatty acids and also quaternised protein hydrolysates, perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctone, olamines and Zinc Omadine, further substances for adjusting the pH, active ingredients such as panthenol, pantothenic acid, allantoin, pyrrolidonecarboxylic acids and salts thereof, plant extracts and vitamins, cholesterol, light stabilisers and UV absorbers, as described, for example, in EP-A-819 422, consistency regulators, such as sugar esters, polyol esters or polyol alkyl ethers, fats and waxes, such as spermaceti, beeswax, montan wax, paraffins, fatty alcohols and fatty acid esters, fatty acid alkanolamides, polyethylene glycols and polypropylene glycols having a molecular weight of from 150 to 50 000, for example such as those described in EP-A-801 942, complexing agents, such as EDTA, NTA and phosphonic acids, swelling and penetration substances, such as polyols and polyol ethers, as listed extensively, for example, in EP-A-962 219, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole, opacifiers, such as latex, pearlising agents, such as ethylene glycol mono- and di-stearate, propellants, such as propane-butane mixtures, $N_2O$, dimethyl ether, $CO_2$ and air, and also antioxidants, for example isoascorbic acid, ascorbic acid, sodium sulfite, thioglycolic acid and thiolactic acid.

The constituents of the aqueous carrier are used in the preparation of the colouring compositions according to the invention in the amounts customary for that purpose; for example emulsifiers are used in concentrations of from 0.5 to 30% by weight and thickeners in concentrations of from 0.1 to 25% by weight of the total colouring composition.

To colour keratin-containing fibres, especially to colour human hair, the colouring compositions are usually applied to the hair in an amount of from 50 to 100 g in the form of the aqueous cosmetic carrier, left on the hair for approximately 30 minutes and then rinsed off or washed off with a commercially available hair shampoo.

The colouring compositions used in accordance with the invention and the optionally used oxidation dye precursors may be applied to the keratin-containing fibres either simultaneously or successively, the order in which they are applied being unimportant.

The colouring compositions used in accordance with the invention and the optionally used oxidation dye precursors may be stored either separately or together, either in a liquid to paste-like preparation (aqueous or non-aqueous) or in the form of a dry powder. When the components are stored together in a liquid preparation, the preparation should be substantially anhydrous in order to reduce reaction of the components. When they are stored separately, the reactive components are intimately mixed with one another only immediately before use. In the case of dry storage, before use a defined amount of hot (from 50 to 80° C.) water is usually added and a homogeneous mixture prepared.

The following Examples serve to illustrate the invention without limiting the invention thereto. Unless specified otherwise, parts and percentages relate to weight. The amounts of dye specified are relative to the material being coloured.

EXAMPLE 1

A) Preparation of Triazenes 43.4 g of 4-chloro-2-amino-1-methylbenzene are mixed with 81 g of 32% hydrochloric acid and cooled to 0° C. Then, over the course of one hour, 75 ml of 4N aqueous sodium nitrite solution are added dropwise, with stirring, the temperature being maintained at from 0 to 5° C. The resulting solution is then added dropwise, over the course of 15 minutes, to an aqueous solution of 30 g of sarcosine and 90 g of sodium carbonate in 250 ml of water at a temperature of 0–5° C. The resulting brown suspension is filtered, the residue is recrystallised from ethanol and dried in air. 66.2 g of 3-methyl-1-(5-chloro-2-methylphenyl)-3-(carboxylmethyl)triazene are obtained in the form of brownish-yellow powder. (Yield: 91%). The compound has the following formula and its $^1$H-NMR spectrum exhibits the chemical shifts indicated.

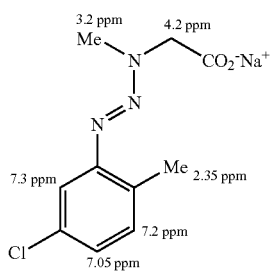

EXAMPLES 2 TO 4

Using a procedure analogous to that described in Example 1, the following compounds are prepared:

| Example | 2 | 3 | 4 |
|---|---|---|---|

Colouring Method A:

A strand of bleached human hair is immersed, for 30 minutes at room temperature, in an aqueous solution containing 0.2M triazene and 0.2M coupling component, which has been adjusted to pH 10.0 using sodium carbonate, ammonia or NaOH. The strand is removed, excess solution is wiped off and the strand is immersed for 5 minutes in a pH 3 buffer solution containing 4% sodium citrate and 2% citric acid. The strand is then thoroughly rinsed using water and, where appropriate, a shampoo solution and is dried. Hair coloured in the shades mentioned is obtained, with outstanding fastness properties, especially fastness to washing properties.

Colouring Method B:

A strand of bleached human hair is immersed, for 30 minutes at room temperature, in an aqueous solution that contains 0.2M triazene, 0.2M coupling component and 0.2M of hydrogen peroxide (6%) and that has been adjusted to a pH in the range pH 9.8–10 using sodium carbonate, ammonia or NaOH. After contact for 5–30 minutes, there is applied to the strand, without its being rinsed, an amount, corresponding to the weight of triazene and coupling component originally used, of a mixture comprising 12.5% strength aqueous citric acid gel, which contains 0.1% by weight of a cationic dye selected from the group of the cationic dyes as disclosed in WO 95/01772 and in WO 01/66646. The strand is then combed through thoroughly, a pH of about 7 being obtained. After contact for 15 minutes, the treated strand is treated again with the above mixture comprising 12.5% strength citric acid gel and 0.1% by weight of a cationic dye selected from the group of the cationic dyes as disclosed in WO 95/01772 and in WO 01/66646 at pH 4 for 5 minutes, rinsed thoroughly with water and then dried. Hair is obtained with outstanding fastness properties, especially fastness to washing and fastness to shampooing properties.

Colouring Method C:

A strand of bleached human hair is immersed, for 30 minutes at room temperature, in an aqueous solution that contains 0.2M triazene, 0.2M coupling component and 0.2 mol of hydrogen peroxide (6%) and that has been adjusted to a pH in the range pH 9.8–10 using sodium carbonate, ammonia or NaOH. After contact for 5–30 minutes, there is applied to the hair, without its being rinsed, an amount, corresponding to the weight of triazene and coupling component originally used, of a 12.5% strength aqueous citric acid gel containing 0.1% by weight of a cationic dye selected from the group of the cationic dyes as disclosed in WO 95/01772 and in WO 01/66646 and 4% sodium citrate; the hair is combed through thoroughly, a pH of about 3 being obtained. Then, after a contact time of 5–30 minutes, the hair is rinsed thoroughly with water and dried. Hair is obtained with outstanding fastness properties, especially good fastening to washing properties.

Colouring Method D:

A strand of bleached human hair is immersed, for 30 minutes at room temperature, in an aqueous solution containing 0.2M triazene, 0.2M coupling component, 0.2 mol of hydrogen peroxide (6%) and from 0.1 to 1% by weight, based on the weight of the triazene and coupling component, of a cationic dye selected from the group of the cationic dyes as described in WO 95/01772 and in WO 01/66646. The strand is then adjusted to a pH in the range pH 9.8–10 using sodium carbonate, ammonia or NaOH. After contact for 5–30 minutes, there is applied to the hair, without its being rinsed, an amount, corresponding to the weight of triazene and coupling component originally used, of a 12.5% strength aqueous citric acid gel and 4% sodium citrate and the hair is combed through thoroughly, a pH of about 3 being obtained. Then, after a contact time of 5–30 minutes, the hair is rinsed thoroughly with water and dried. Hair is obtained with outstanding fastness properties, especially good fastness to washing properties.
| Triazene | Coupler | Hair colour |
|---|---|---|
| Example 5: 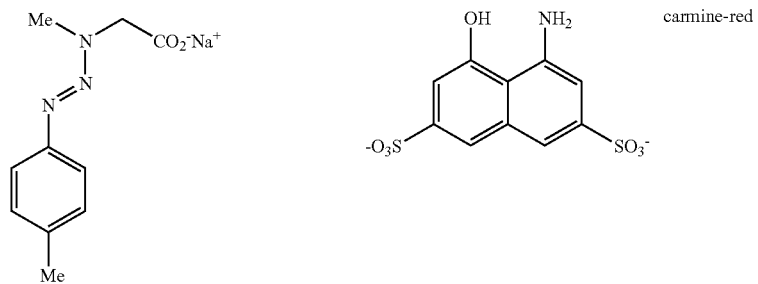 | | carmine-red |
| Example 6: 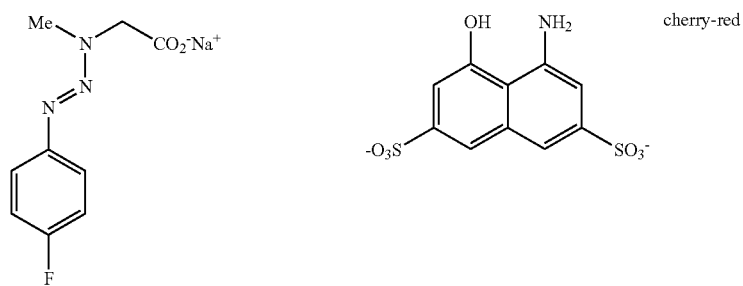 | | cherry-red |
| Example 7: 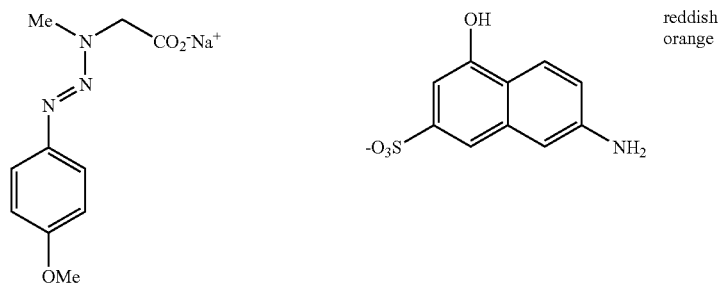 | | reddish orange |
| Example 8: 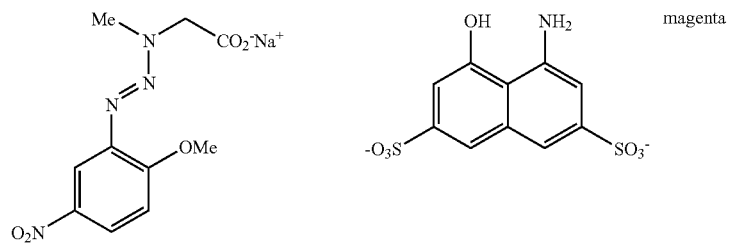 | | magenta |

-continued
| Triazene | Coupler | Hair colour |
|---|---|---|
| Example 9: 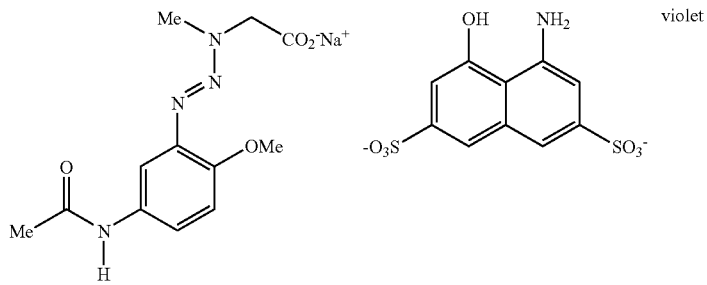 | | violet |
| Example 10: 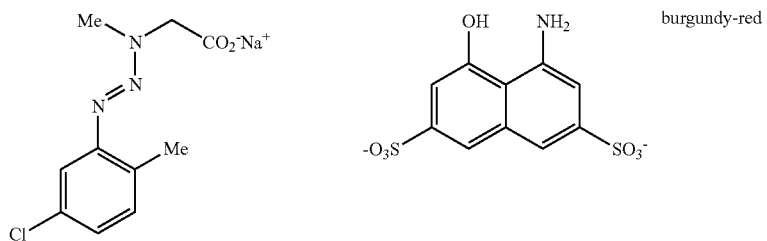 | | burgundy-red |
| Example 11: 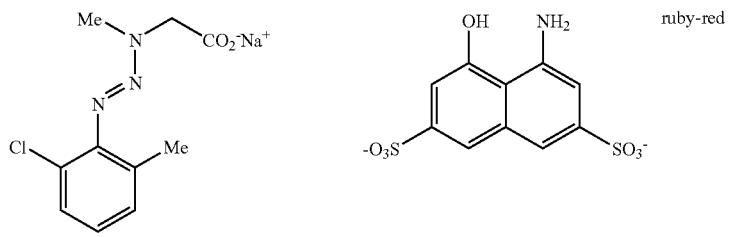 | | ruby-red |
| Example 12: 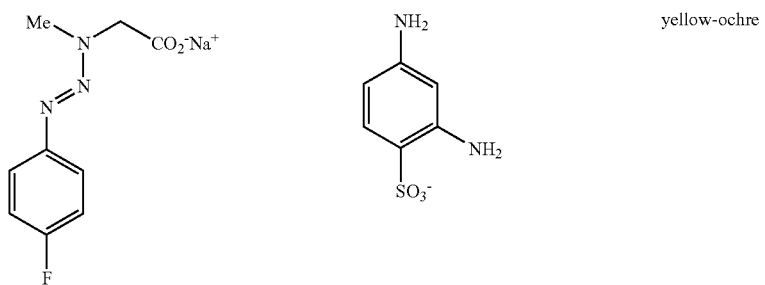 | | yellow-ochre |
| Example 13: 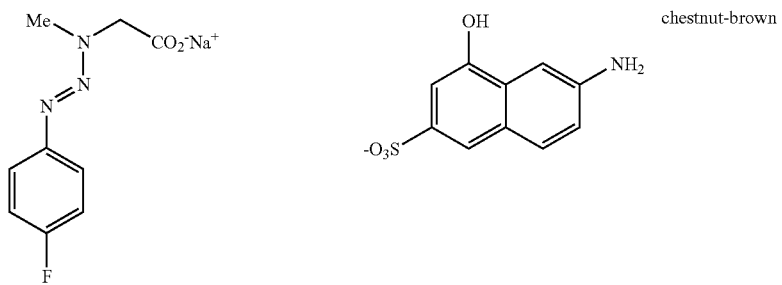 | | chestnut-brown |

| Triazene | Coupler | Hair colour |
|---|---|---|
| Example 14: | | |
| 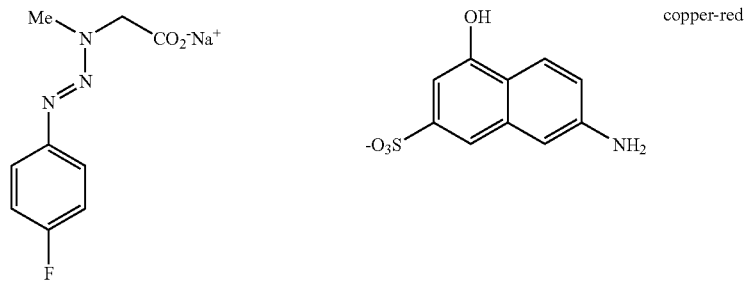 | | copper-red |
| Example 15: | | |
| 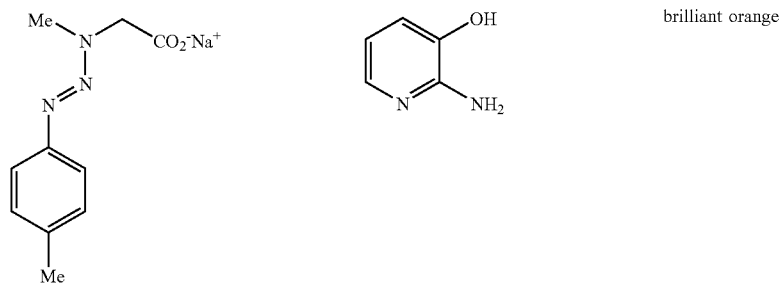 | | brilliant orange |
| Example 16: | | |
| 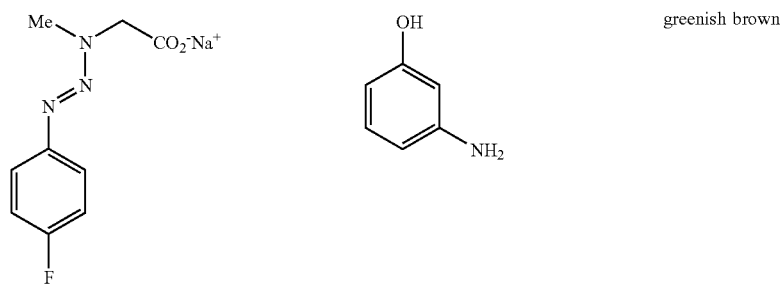 | | greenish brown |
| Example 17: | | |
| 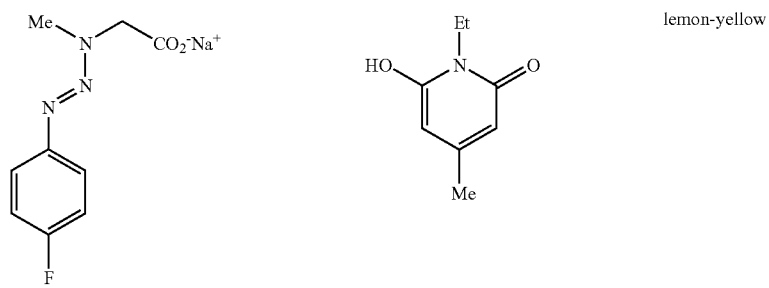 | | lemon-yellow |

| Triazene | Coupler | Hair colour |
|---|---|---|
Example 18:
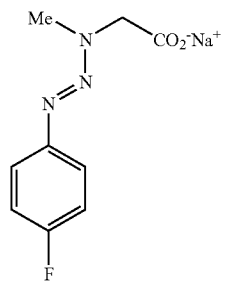 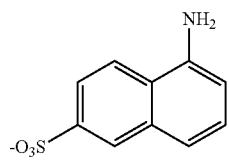  reddish orange
Example 19:
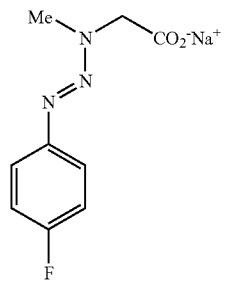 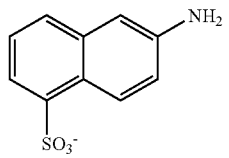  golden-yellow
Example 20:
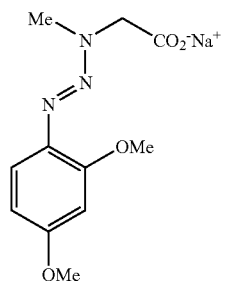 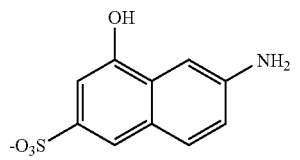  copper-red
Example 21:
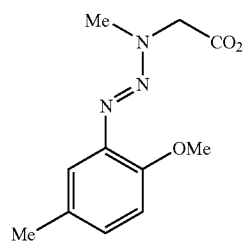 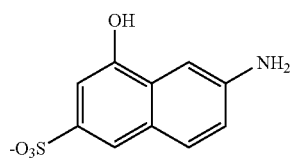  copper-red -continued
| Triazene | Coupler | Hair colour |
|---|---|---|
| Example 22: 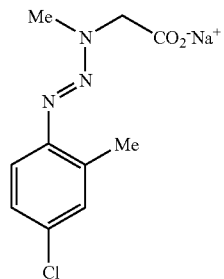 | 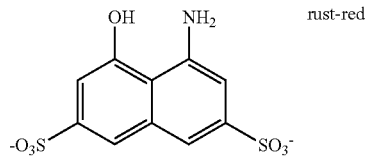 | rust-red |
| Example 23: 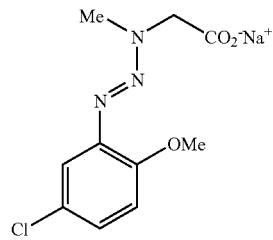 | 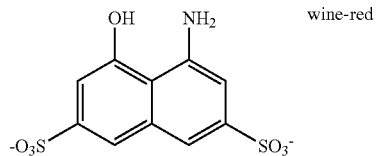 | wine-red |
| Example 24: 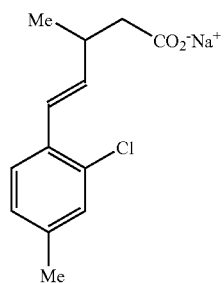 | 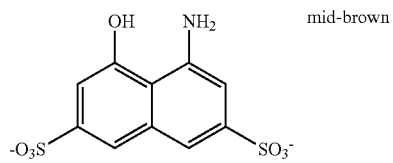 | mid-brown |
| Example 25: 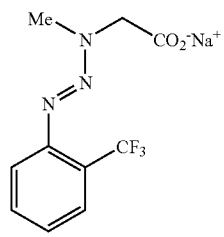 | 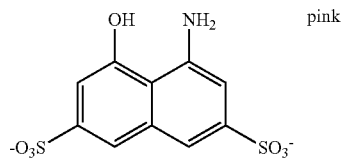 | pink |
| Example 26: 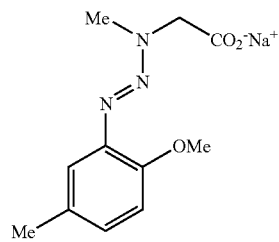 | 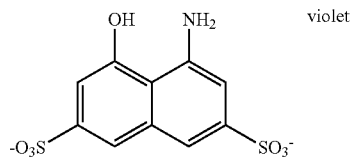 | violet |

-continued
| Triazene | Coupler | Hair colour |
|---|---|---|
Example 27:
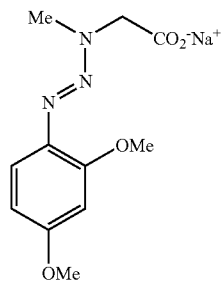 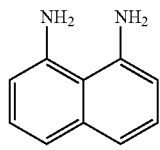 blue-black
Example 28:
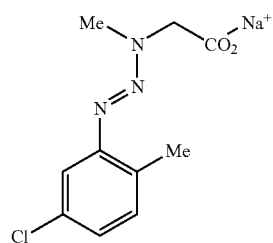 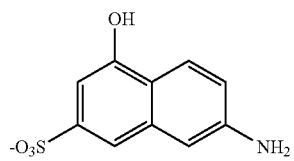 copper-red
Example 29:
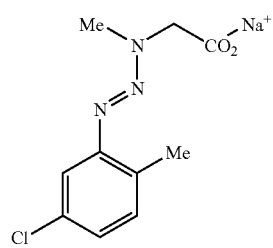 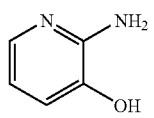 copper-coloured
Example 30:
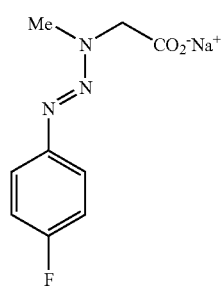 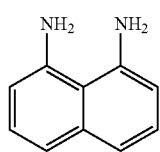 purple
Example 31:
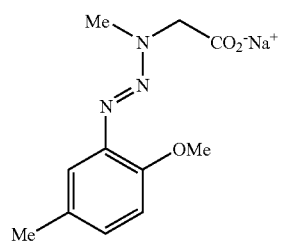 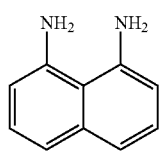 blue -continued
| Triazene | Coupler | Hair colour |
|---|---|---|
| Example 32: 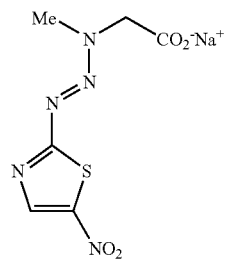 | 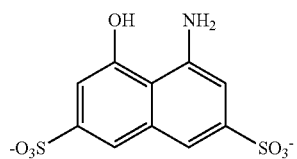 | blue |
| Example 33: 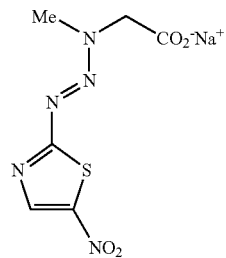 | 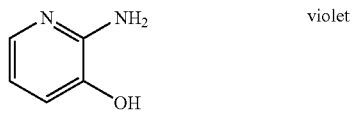 | violet |
| Example 34: 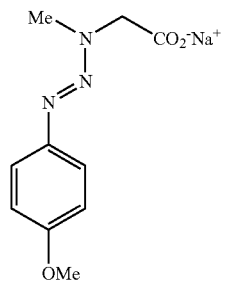 | 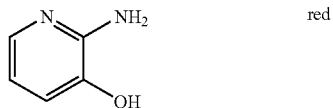 | red |
| Example 35: 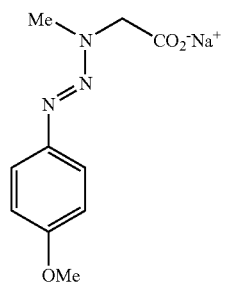 | 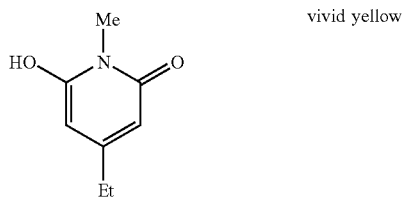 | vivid yellow |
| Example 36: 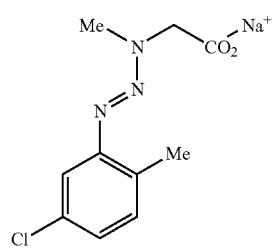 | 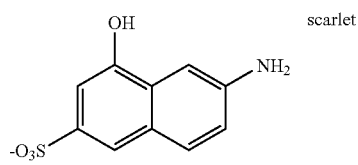 | scarlet |

-continued
| Triazene | Coupler | Hair colour |
|---|---|---|
| Example 37: 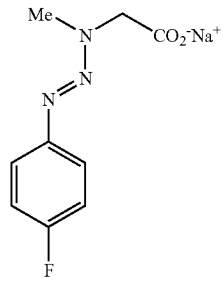 | 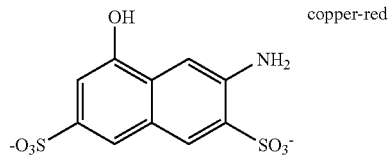 | copper-red |
| Example 38: 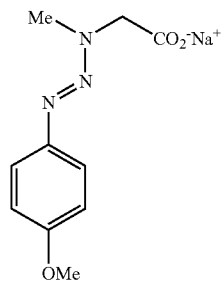 | 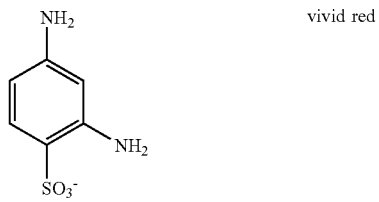 | vivid red |
| Example 39: 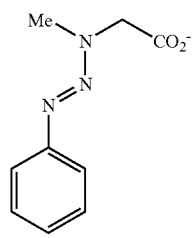 | 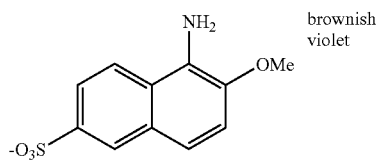 | brownish violet |
| Example 40: 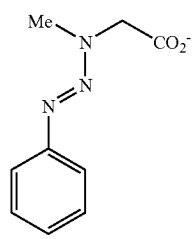 | 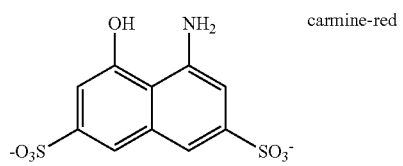 | carmine-red |
| Example 41: 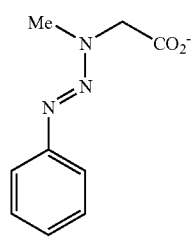 | 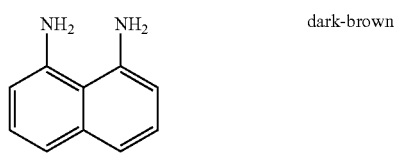 | dark-brown |

-continued
| Triazene | Coupler | Hair colour |
|---|---|---|
| Example 42: 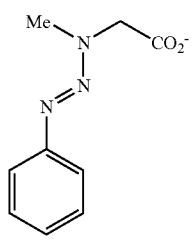 | 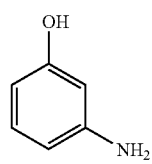 | brownish orange |
| Example 43: 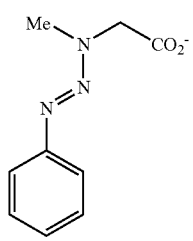 | 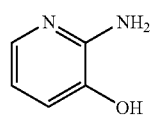 | vivid red |
| Example 44: 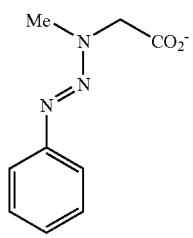 | 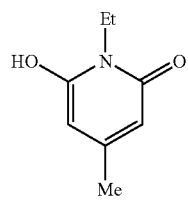 | vivid yellow |
| Example 45: 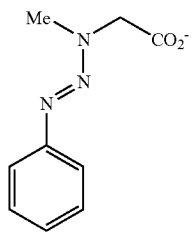 | 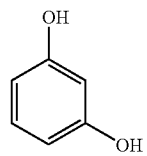 | yellowish orange |
| Example 46: 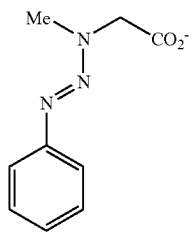 | 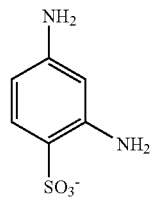 | reddish orange |

| Triazene | Coupler | Hair colour |
|---|---|---|
Example 47:
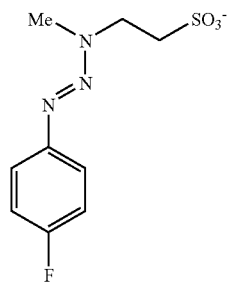 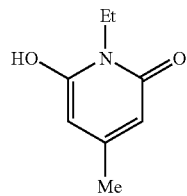 lemon-yellow
Example 48:
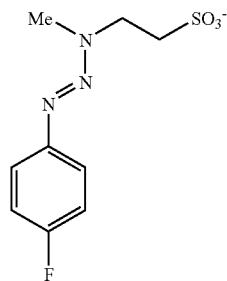 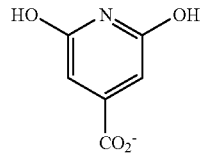 straw-yellow
Example 49:
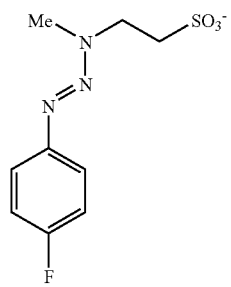 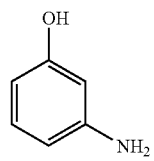 brownish orange
Example 50:
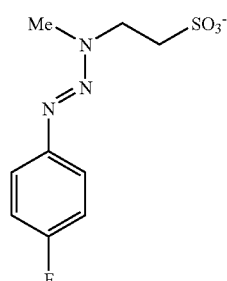 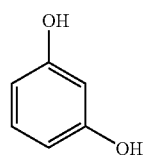 dull orange

| Triazene | Coupler | Hair colour |
|---|---|---|
Example 51:
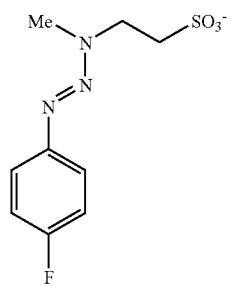 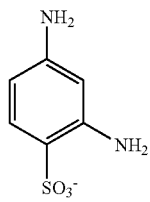 reddish orange
Example 52:
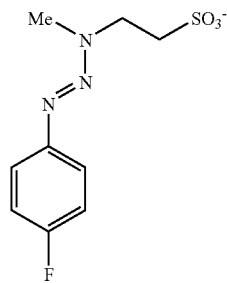 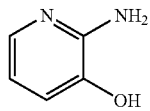 vivid red
Example 53:
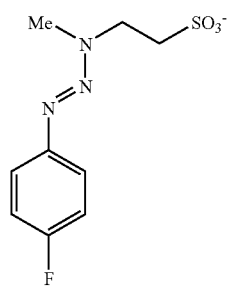 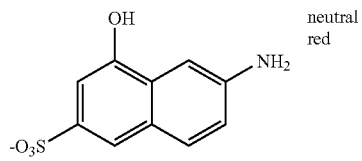 neutral red
Example 54:
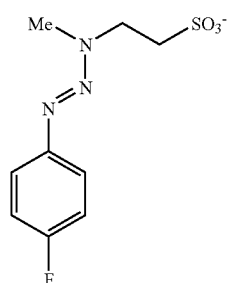 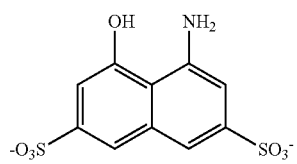 cherry-red -continued
| Triazene | Coupler | Hair colour |
|---|---|---|
Example 55:
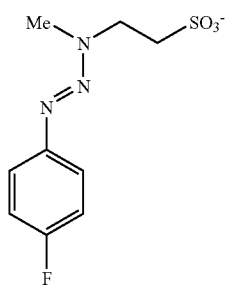 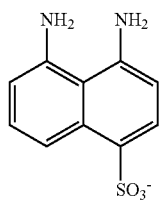  purplish black
Example 56:
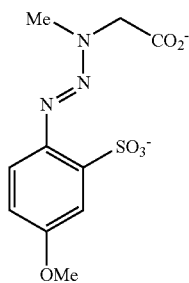 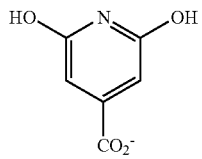  vivid yellow
Example 57:
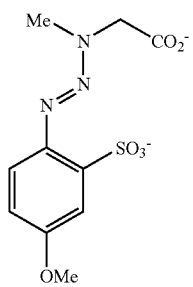 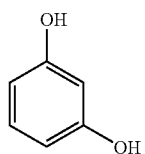  dull yellow
Example 58:
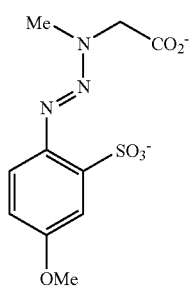 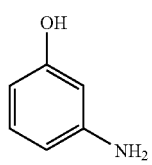  greenish brown

| Triazene | Coupler | Hair colour |
|---|---|---|
Example 59:
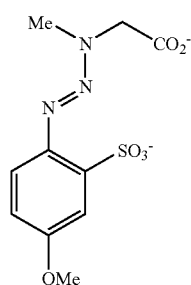 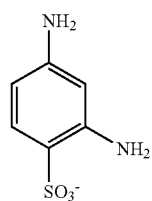  yellowish orange
Example 60:
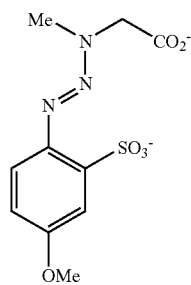 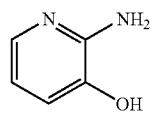  ruby-red
Example 61:
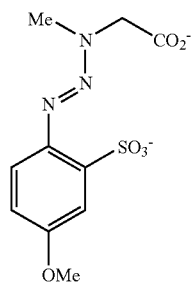 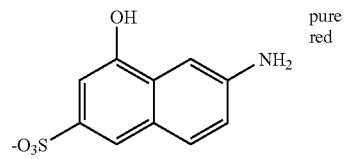  pure red
Example 62:
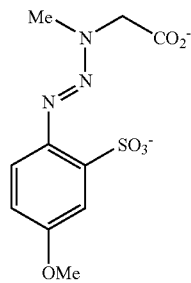 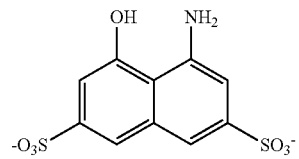  reddish purple

| Triazene | Coupler | Hair colour |
|---|---|---|
Example 63:
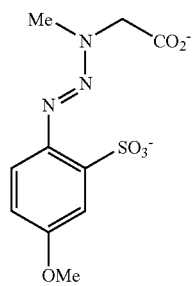 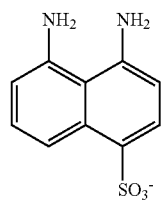 violet
Example 64:
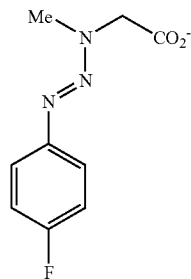 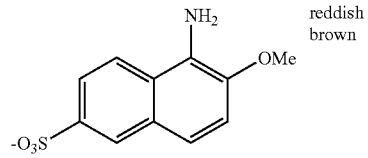 reddish brown
Example 65:
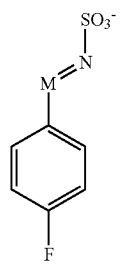 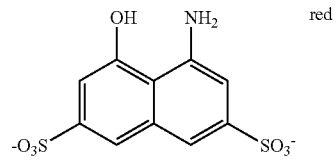 red
Example 66:
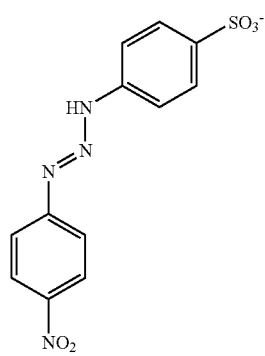 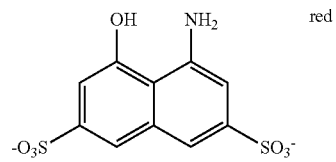 red

| Triazene | Coupler | Hair colour |
|---|---|---|

Example 67:

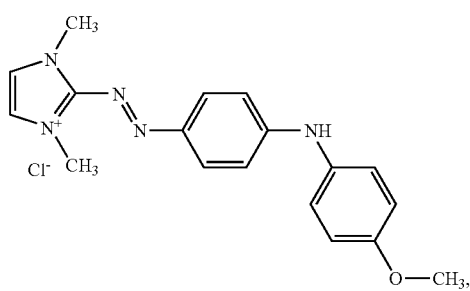

red

EXAMPLE 68

A strand of bleached human hair is treated with a mixture of equal parts by weight—5 g in each case—of 6% hydrogen peroxide solution and of composition A.

| Composition A: | |
|---|---|
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| 2,5-diaminotoluene sulfate | 0.7 |
| 4-amino-2-hydroxytoluene | 0.5 |
| 2,5,6-triamino-4-hydroxypyrimidine sulfate | 0.2 |
| sodium sulfite | 1.0 |
| ascorbic acid | 0.5 |
| triazene of Example 30 | 9.32 |
| coupler of Example 30 | 11.52 |
| composition A: pH | 9.8 |
| water | ad 100 |

After contact for 15 minutes at room temperature, about 22° C., 10 g of a mixture of a 12.5% strength aqueous citric acid gel containing 0.1% by weight of a violet dye of the following formula which is prepared analogously to WO 01/66646, Example 4, is applied to the strand. The strand is then combed through, whereupon a pH of about 7 is achieved. After contact for a further 15 minutes, the strand is again treated with 10 g of the above mixture of citric acid gel and violet dye, whereupon a pH of about 4 is achieved. The mixture is allowed to act for 5 minutes at pH 4 and the strand is then washed with water and shampoo and then again with water. The strand is then dried.

A strong, intense, striking violet coloration having good fastness to washing and fastness to rubbing properties is obtained.

EXAMPLE 69

A strand of medium-blond human hair is coloured with a mixture of equal parts by weight—5 g in each case—of 6% hydrogen peroxide solution and of composition A according to Example 68.

The mixture is allowed to act on the strand for 30 minutes at room temperature, about 22° C. 10 g of a mixture of a 2% strength aqueous citric acid gel containing 0.1% by weight of a violet dye according to the above formula in Example 68, and 4% sodium citrate, are then applied to the strand. The strand is then combed through, whereupon a pH of about 3 is achieved. After contact for 5 minutes, the strand is thoroughly rinsed and then dried.

A strong, intense, striking violet coloration having good fastness to washing and fastness to rubbing properties is obtained.

EXAMPLE 70

A strand of bleached human hair is coloured with a mixture of equal parts by weight—5 g in each case—of 6% hydrogen peroxide solution and of composition B.

| Composition B: | |
|---|---|
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |

-continued

| Composition B: | |
|---|---|
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 30 | 9.32 |
| coupler of Example 30 | 11.52 |
| composition B: pH | 9.8 |
| water | ad 100 |

The mixture is allowed to act on the strand for 30 minutes at about 22° C. 10 g of a mixture of a 2% strength aqueous citric acid gel containing 0.1% by weight of a violet dye according to the above formula in Example 68, and 4% sodium citrate, are then applied to the strand. The strand is then combed through, whereupon a pH of about 3 is achieved. After contact for 5 minutes, the strand is thoroughly rinsed and then dried.

A strong, intense, striking violet coloration having good fastness to washing and fastness to rubbing properties is obtained.

EXAMPLE 71

A strand of blond undamaged human hair is coloured with a mixture of equal parts by weight—5 g in each case—of 6% hydrogen peroxide solution and of composition C.

| Composition C: | |
|---|---|
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| violet dye of Example 68 | 0.2 |
| triazene of Example 30 | 9.32 |
| coupler of Example 30 | 11.52 |
| composition C: pH | 9.8 |
| water | ad 100 |

The mixture is allowed to act on the strand for 30 minutes at about 22° C. 10 g of a mixture of a 2% strength aqueous citric acid gel containing 0.1% by weight of a violet dye according to the above formula in Example 68, and 4% sodium citrate, are then applied to the strand; the latter is then combed through, whereupon a pH of about 3 is achieved. After contact for 5 minutes, the strand is thoroughly rinsed and then dried.

A strong, intense, striking violet coloration having good fastness to washing and fastness to rubbing properties is obtained.

EXAMPLE 72

A strand of blond undamaged human hair is coloured with 10 g of composition D.

| Composition D: | |
|---|---|
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| violet dye of Example 68 | 0.2 |
| triazene of Example 30 | 4.66 |
| coupler of Example 30 | 5.76 |
| composition D: pH | 10 |
| water | ad 100 |

The mixture is allowed to act on the strand for 30 minutes at about 22° C. 10 g of a mixture of a 2% strength aqueous citric acid gel containing 4% sodium citrate are then applied to the strand; the latter is then combed through, whereupon a pH of about 3 is achieved. After contact for 5 minutes, the strand is thoroughly rinsed and then dried. A strong, intense, striking violet coloration having good fastness to washing and fastness to rubbing properties is obtained.

EXAMPLE 73

A strand of blond undamaged human hair is coloured with 10 g of composition E.

| Composition E | |
|---|---|
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 36 | 4.66 |
| coupler of Example 36 | 5.76 |
| composition E: pH | 10 |
| water | ad 100 |

The mixture is allowed to act on the strand for 30 minutes at about 22° C. Then 10 g of a mixture of a 2% strength aqueous citric acid gel containing 0.1% by weight of a red dye of the following formula

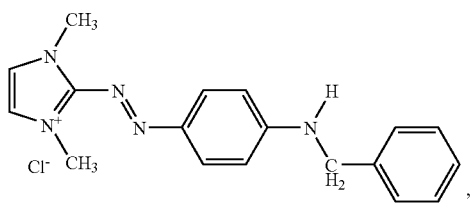

which can be prepared, for example, as described in WO 01/11708, according to Preparation Example 6, compound of formula 106,
and 4% sodium citrate, are applied to the strand and then combed through, whereupon a pH of about 3 is achieved. After contact for 5 minutes, the strand is thoroughly rinsed and then dried.

A strong, intense, striking scarlet coloration having good fastness to washing and fastness to rubbing properties is obtained.

EXAMPLE 74

A strand of blond undamaged human hair is coloured with 10 g of composition F.

| Composition F | |
|---|---|
| cetyl stearyl alcohol | 11.00 |
| oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| silica | 0.1 |
| triazene of Example 36 | 5.3 |
| coupler of Example 36 | 5.2 |
| composition F: pH | 10 |
| water | ad 100 |

After contact for 30 minutes, without being washed out, a dye mixture known from U.S. Pat. No. 6,248,314 and having the following composition:

| Black Color No. 401 | 0.1 |
|---|---|
| Purple Color 401 | 0.05 |
| Orange Color No. 205 | 0.1 |
| benzyl alcohol | 2.0 |
| ethylene carbonate | 10 |
| propylene carbonate | 15 |
| ethanol | 10 |
| lactic acid | 3.5 |
| sodium carbonate solution | of pH 2.9 |
| hydroxyethyl cellulose | 1.5 |
| water | ad 100 | is applied to the hair. The hair is then combed through thoroughly, whereupon its pH becomes about 3. Then, after a contact period of 15 minutes, the hair is rinsed thoroughly with water and dried.

A strong, intense, striking red coloration having good fastness to washing and fastness to rubbing properties is obtained.

EXAMPLE 75

A strand of blond undamaged human hair is coloured with 10 g of a composition comprising compositions A and B.

| Compositions | A | B | C |
|---|---|---|---|
| cetyl stearyl alcohol | 11.00 | 11.00 | 11.00 |
| oleth-5 | 5.0 | 5.0 | 5.0 |
| oleic acid | 2.5 | 2.5 | 2.5 |
| stearic acid monoethanolamide | 2.5 | 2.5 | 2.5 |
| coconut fatty acid monoethanolamide | 2.5 | 2.5 | 2.5 |
| sodium lauryl sulfate | 1.7 | 1.7 | 1.7 |
| 1,2-propanediol | 1.0 | 1.0 | 1.0 |
| ammonium chloride | 0.5 | 0.5 | 0.5 |
| EDTA, tetrasodium salt | 0.2 | 0.2 | 0.2 |
| perfume | 0.4 | 0.4 | 0.4 |
| wheat protein hydrolysate | 0.2 | 0.2 | 0.2 |
| silica | 0.1 | 0.1 | 0.1 |
| 2,5-diaminotoluene sulfate | | | 0.7 |
| 4-amino-2-hydroxytoluene | | | 0.5 |
| 2,5,6-triamino-4-hydroxypyrimidine sulfate | | | 0.2 |
| sodium sulfite | | | 1.0 |
| ascorbic acid | | | 0.5 |
| triazene of Example 30 | 9.32 | | |
| coupler of Example 30 | | 11.52 | |
| composition: pH | 10 | 10 | 10 |
| water | ad 100 | ad 100 | ad 100 |

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking coloration having good fastness to washing and fastness to rubbing properties is obtained.

EXAMPLE 76

A strand of blond undamaged human hair is coloured with a mixture of 15 g of 6% hydrogen peroxide solution and a composition consisting of 5 g each of compositions A, B and C according to Example 75.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking coloration having good fastness to washing and fastness to rubbing properties is obtained.

What is claimed is:
1. A method of colouring hair, which comprises applying to the hair being coloured, in any order successively, or simultaneously,
  a capped diazonium compound and
  a water-soluble coupling component
  a) under alkaline conditions and optionally in the presence of a further dye, and then subjecting the hair being coloured to treatment with acid, or
  b) under alkaline conditions, and then subjecting the hair being coloured to treatment with acid, optionally in the presence of a further dye, wherein there is used as the capped diazonium compound an antidiazoate of formula

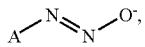 (1)

a diazosulfonate of formula

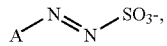 (2)

a diazine of formula

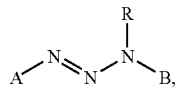 (3)

or a cyclic triazene of formula

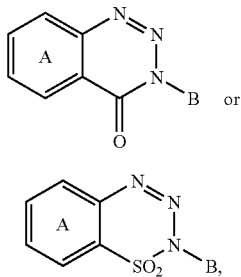 (4)

(5)

wherein
A is the organic residue of an unsubstituted or substituted aromatic or heterocyclic amine and
B is the radical of an unsubstituted or substituted, water-soluble aliphatic or aromatic amine,
wherein at least one of the above groups must contain a radical imparting water solubility.

2. A method according to claim 1, which comprises bringing the hair being coloured into contact with
a capped diazonium compound and
a water-soluble coupling component,
in any desired order successively, or simultaneously,
c) under alkaline conditions in the presence of an oxidising agent and optionally in the presence of a further dye, and
then subjecting the hair being coloured to treatment with acid, or
d) under alkaline conditions, and
then subjecting the hair being coloured to treatment with acid, optionally in the presence of a further dye.

3. A method according to claim 1, wherein the radical imparting water solubility is $SO_3H$, COOH, OH or a quaternised ammonium radical of formula

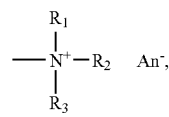 (6)

wherein $R_1$, $R_2$ and $R_3$ are each independently of the others unsubstituted or substituted alkyl and An is an anion.

4. A method according to claim 1, wherein A is the organic residue of an unsubstituted or substituted aminobenzene, 1- or 2-aminonaphthalene, 2-aminothiophene, 2-amino-1,3-thiazole, 5-amino-1,2-thiazole, 2-amino-1,3-benzothiazole, 1-amino-2,3-benzothiazole, 2-aminoimidazole, 2-amino-1,3,4-thiadiazole, 2-amino-1,3,5-thiadiazole, 2-amino-1,3,4-triazole, 3-, 7- or 8-aminopyrazole, 2-aminobenzimidazole, 2-aminobenzopyrazole, 2- or 4-aminopyridine, 2-, 3-, 4-, 7- or 8-aminoquinoline, 2-aminopyrimidine and 3-aminoisoxazole, 5-aminoquinoline, 4-aminodiphenylamine, 2-aminodiphenyl ether or 4-aminoazobenzene.

5. A method according to claim 4, wherein the radical A is unsubstituted or is mono- or poly-substituted by $C_1$–$C_4$alkyl, $C_1$–$C_4$alkoxy, $C_1$–$C_4$alkylthio, halogen, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkylcarbonylamino, $C_1$–$C_4$alkoxysulfonyl or by di-(hydroxy-$C_1$–$C_4$alkyl)-aminosulfonyl.

6. A method according to claim 1, wherein B is the radical of an aliphatic amine carrying a carboxylic acid or sulfonic acid group and optionally carrying further substituents.

7. A method according to claim 6, wherein B is the radical of an aniline or aminonaphthalene compound carrying a carboxylic acid or sulfonic acid group and optionally carrying further substituents.

8. A method according to claim 1, wherein there is used as the coupling component an unsubstituted or substituted acylacetarylamide, phenol, naphthol, pyridine, quinolone, pyrazole, indole, diphenylamine, aniline, aminopyridine, pyrimidone, naphthylamine, aminothiazole, thiophene or hydroxypyridine.

9. A method according to claim 8, wherein a coupling component mono- or poly-substituted by amino, alkylamino, dialkylamino, halogen, alkyl, alkoxy, phenyl, naphthyl or by aryloxy is used.

10. A method according to claim 8, wherein a coupling component mono- or poly-substituted by a group imparting water solubility, is used.

* * * * *